United States Patent
Schleider

(10) Patent No.: US 8,753,706 B2
(45) Date of Patent: *Jun. 17, 2014

(54) EDIBLE MIX AND METHOD OF MAKING THE SAME

(75) Inventor: M. David Schleider, Towson, MD (US)

(73) Assignee: Grand Brands LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/566,255

(22) Filed: Aug. 3, 2012

(65) Prior Publication Data

US 2012/0301600 A1    Nov. 29, 2012

Related U.S. Application Data

(63) Continuation of application No. 12/818,978, filed on Jun. 18, 2010, now Pat. No. 8,236,365, which is a continuation of application No. 10/842,542, filed on May 11, 2004, now Pat. No. 7,744,943.

(60) Provisional application No. 60/469,638, filed on May 12, 2003.

(51) Int. Cl.
*A23L 2/00* (2006.01)

(52) U.S. Cl.
USPC ............................ 426/590; 426/591; 426/599

(58) Field of Classification Search
USPC .......................................... 426/590, 591, 599
See application file for complete search history.

(56) References Cited

U.S. PATENT DOCUMENTS

| | | | | |
|---|---|---|---|---|
| 4,113,865 A | * | 9/1978 | Dondi et al. | 514/163 |
| 5,296,249 A | * | 3/1994 | Todd, Jr. | 426/541 |
| 5,792,507 A | * | 8/1998 | Kato et al. | 427/2.18 |
| 6,123,980 A | * | 9/2000 | Pearson et al. | 426/658 |
| 6,902,751 B1 | * | 6/2005 | Schleifenbaum et al. | 426/89 |
| RE40,059 E | * | 2/2008 | Pacifico et al. | 427/213.3 |
| 7,744,943 B2 | * | 6/2010 | Schleider | 426/590 |
| 8,236,365 B2 | * | 8/2012 | Schleider | 426/590 |
| 2002/0001656 A1 | * | 1/2002 | Mason et al. | 426/565 |

OTHER PUBLICATIONS

Lemon Flavor Crystals (online), Diamond Crystal Brands, Inc., [retrieved on Oct. 29, 2000]Retrieved from the internet:<URL: http://www.diamoncrystal.com/pack/misc/misc-05.html>.*
Kimball, C. 2001. Kitchen Detective: Perfect puckerless lemonade recipe; Change the usual by using lime instead of lemons. Charleston Daily Mail, Charleston, WV. Apr. 4, 2001. p. 3D.*

* cited by examiner

*Primary Examiner* — Carolyn Paden
(74) *Attorney, Agent, or Firm* — Ballard Spahr LLP

(57) ABSTRACT

An edible mix includes granulated lemon juice solids, granulated citric acid or granulated malic acid, and encapsulated natural lemon oil. In one embodiment, the edible mix also includes granulated maltodextrin, granulated ascorbic acid, and granulated lactose. In one embodiment, the components of the edible mix are mechanically mixed together to form a substantially homogeneous composition. In one embodiment, several of the components are blended by an agglomeration method.

10 Claims, No Drawings

EDIBLE MIX AND METHOD OF MAKING THE SAME

CROSS-REFERENCE TO RELATED APPLICATIONS

This application is a continuation of U.S. patent application Ser. No. 12/818,978 filed on Jun. 18, 2010 now U.S. Pat. No 8,236,365, which is a continuation of U.S. patent application Ser. No. 10/842,542 filed on May 11, 2004 now U.S. Pat. No. 7,744,943, which is based on and claims priority to U.S. Provisional Patent Application No. 60/469,638, titled "Granulated Natural Lemon Condiment," filed on May 12, 2003, the disclosure of which are incorporated herein by reference in their entireties.

BACKGROUND

The invention relates generally to edible mixes and, more particularly, to a natural lemon edible mix.

People generally enjoy a slight taste of lemon in their foods and beverages. For example, it is common for a person to squeeze a portion of a freshly cut lemon into a beverage, such as a glass of water or a soft drink. Similarly, it is common for a person to squeeze a portion of a freshly cut lemon onto a food item, such as a fish or seafood, prior to eating the food item. Often times, however, a person may have difficulty in locating a fresh lemon to squeeze in their beverage or onto their food items. Therefore, lemon-flavored mixes, which may be placed in beverages or on food items, have been created. These known lemon-flavored mixes, however, contain various preservatives, sweeteners, spices and/or additional chemicals. Additionally, large quantities of the known lemon-flavored mixes have to be added to a beverage or onto a food item to provide a person with sufficient lemon favor. Finally, these known lemon-flavored mixes tend to clump together and do not pour well out of a dispenser, such as a packet or a shaker type dispenser.

Thus, a need exists for an edible mix that tastes and smells like a lemon and does not include preservatives. Additionally, a need exists for an edible mix that does not require a person to use a large quantity of the edible mix to achieve a sufficient lemon taste. Finally, a need exists for an edible mix that tastes and smells like a lemon and can be easily poured out of a dispenser, such as a packet or a shaker type dispenser.

SUMMARY OF THE INVENTION

An edible mix includes granulated lemon juice solids that has dehydrated lemon juice, granulated citric acid or granulated malic acid, and encapsulated natural lemon oil. In one embodiment, the edible mix also includes granulated maltodextrin, granulated ascorbic acid, and granulated lactose. In one embodiment, the components of the edible mix are mechanically mixed together to form a substantially homogeneous composition. In one embodiment, several of the components are blended by an agglomeration method.

DETAILED DESCRIPTION

An edible mix includes granulated lemon juice solids that has dehydrated lemon juice, granulated citric acid or granulated malic acid, and encapsulated natural lemon oil. In one embodiment, the edible mix also includes granulated maltodextrin, granulated ascorbic acid, and granulated lactose. In one embodiment, the components of the edible mix are mechanically mixed together to form a substantially homogeneous composition. In one embodiment, several of the components are blended by an agglomeration method.

The term "edible" as used herein is a broad term and includes anything that can be consumed, eaten, drank, or otherwise ingested. Accordingly, an edible mix is a mixture of components that may be in a solid form, a dissolved or liquid form, a crystal form, or any other form and may be consumed, eaten, drank, other otherwise ingested.

In an edible mix that provides a lemon scent and lemon taste closely replicating that from an actual lemon, there are several ingredients, including dehydrated lemon juice, lemon oil, and citric acid. One way that this can be accomplished is by an edible mix that has a relatively high ratio of lemon oil to dehydrated lemon juice. Lemon oil, however, often spoils relatively easily and quickly. Accordingly, a substantial amount preservatives are added to known lemon-flavored mixes to prevent the lemon oil from spoiling. Some embodiments of this invention, however, relate to an edible mix that includes lemon oil that is encapsulated, thereby preventing rapid spoiling of the lemon oil without the use of a substantial amount of preservative. In other words, a small quantity (relative to known lemon-flavored mixes) of the edible mix can provide a beverage or a food item with a lemon scent and lemon taste that more closely replicates that from an actual lemon.

Another way to produce an edible mix that has a lemon scent and a lemon taste similar to that from an actual lemon is to provide an edible mix that has a relatively high weight ratio of lemon oil to citric acid. Accordingly, in some embodiments of this invention, the edible mix includes a relatively high weight ratio of lemon oil to citric acid.

The edible mix according to one embodiment of the invention includes granulated lemon juice solids, granulated citric acid, and encapsulated natural lemon oil. The granulated lemon juice solids comprise of lemon juice that has been derived from a lemon, added with a carrier (e.g., maltodextrin or corn syrup), and then spray dried or freeze dried. In other words, the granulated lemon juice solids include dehydrated lemon juice. The granulated lemon juice solids are placed in a granulated form by spray drying or freeze drying. In one embodiment, "18+1" granulated lemon juice solids are used. An "18+1" lemon juice solid includes 18% by weight dehydrated lemon juice, 1% by weight natural lemon oil, and 81% by weight carrier or binder. In another embodiment, a "45-55" granulated lemon juice solid is used. A "45-55" granulated lemon juice solid includes 45% by weight dehydrated lemon juice and 55% by weight carrier or binder. Such granulated lemon juice solids can be acquired, for example, from Sunkist under the product name dehydrated lemon juice powder.

Citric acid has a chemical formula of $C_6H_8O_7$. Such granulated citric acid can be acquired, for example, from Archer Daniel Midland ("ADM") under the product name anhydrous citric acid.

In one embodiment, the edible mix includes granulated malic acid rather than granulated citric acid. The chemical formula for malic acid is $C_4H_6O_5$. Such granulated malic acid can be acquired from ADM under the product name anhydrous malic acid.

Natural lemon oil is the oil that is excreted from an actual lemon. The term "natural" is used herein to mean anything extractable from a lemon. In other words, natural lemon oil is oil that comes directly from an actual lemon. Natural lemon oil does not include any preservatives or other ingredients or components that do not come directly from a lemon. Additionally, natural lemon oil does not include any synthesized or man-made substance unless such substance is extractable from a lemon.

In some embodiments, the natural lemon oil is encapsulated within a capsule, which excludes spray drying techniques. In one embodiment, the capsule does not let air from outside the capsule contact the lemon oil disposed within the capsule. In other words, the capsule is air tight. In another embodiment, the capsule is substantially air tight. The capsule or shell prevents the natural lemon oil from spoiling. Accordingly, because the capsule prevents the natural lemon oil from spoiling, the use of the encapsulated natural lemon oil obviates the need to use a preservative in the edible mix and, therefore, allows for a higher concentration of natural lemon oil. Additionally, the capsule prevents the natural lemon oil from being cross-contaminated with other ingredients. In one embodiment, the capsule is configured to dissolve when the capsule is placed in a warm, moist environment or when the capsule contacts a liquid, such as water, a soft drink, or moisture occurring in food items. Thus, when the encapsulated natural lemon oil is disposed within a beverage or on a food item, such as a fish, the capsule dissolves and the natural lemon oil is exposed to provide a lemon scent and contribute to a lemon taste of the beverage or the food item.

In one embodiment, the encapsulated natural lemon oil is extruded encapsulated natural lemon oil. In other words, the natural lemon oil is encapsulated by an extrusion method. For example, in one embodiment the natural lemon oil is encapsulated using an extruder, such as a cooker extruder. In such an embodiment, the capsule material is heated to form a molten material and the natural lemon oil is mixed with the molten capsule material. The mixture of the molten capsule material and the natural lemon oil is extruded and cooled. As the extruded material cools, the capsule material hardens and entraps the natural lemon oil.

In one embodiment, the capsules that encapsulate or contain the natural lemon oil are made of a carbohydrate matrix. Such extruded encapsulated natural lemon oil can be acquired, for example, from Firmenich under the product name Duraromes. In one embodiment, the weight of the capsule is about 90% of the total weight of the capsule and the natural lemon oil. In other words, the natural lemon oil is about 10% of the total weight of the capsule and the natural lemon oil. In another embodiment, the natural lemon oil is about 7% of the total weight of the capsule and the natural lemon oil. In a further embodiment, the natural lemon oil is between 7% and 10% of the total weight of the capsule and the natural lemon oil. In yet a further embodiment, the natural lemon oil is between 30% and 40% of the total weight of the capsule and the natural lemon oil.

In one embodiment of the edible mix, the weight of the natural lemon oil (including the encapsulated natural lemon oil and any natural lemon oil in the granulated lemon juice solids, for example if an "18+1" lemon juice solid is used) is 0.85% of the total weight of the edible mix. In another embodiment, the weight of the natural lemon oil is about 0.62% of the total weight of the edible mix. In another embodiment, the weight of the natural lemon oil is between 0.60% and 0.90% of the total weight of the edible mix. Accordingly, because the ratio of the natural lemon oil to the total weight of the edible mix is relatively high (as compared to known lemon-flavored mixes), a relatively small quantity (as compared to known lemon-flavored mixes) of the edible mix is required to achieve a lemon scent and a lemon taste in a beverage or a food item.

In one embodiment, the weight ratio of the natural lemon oil to the dehydrated lemon juice is about 0.70 to 1. In another embodiment, the weight ratio of the natural lemon oil to the dehydrated lemon juice is about 0.47 to 1. In a further embodiment, the weight ratio of the natural lemon oil to the dehydrated lemon juice is between 0.40 and 0.75 to 1. Accordingly, because the ratio of the natural lemon oil to dehydrated lemon juice is relatively high (as compared to known lemon-flavored mixes), a relatively small quantity (as compared to known lemon-flavored mixes) of the edible mix can achieve a lemon scent and a lemon taste in a beverage or a food item.

In other embodiments, the edible mix includes less natural lemon oil. Accordingly, in one embodiment, the weight ratio of the natural lemon oil to the dehydrated lemon juice is about 1 to 15. In another embodiment, the weight ratio of the natural lemon oil to the dehydrated lemon juice is about 1 to 10. In yet another embodiment, the weight ratio of the natural lemon oil to the dehydrated lemon juice is about 1 to 5. Although the above embodiments have been described as having natural lemon oil, in alternative embodiments, the edible mix includes non-natural lemon oil.

In one embodiment, the weight ratio of the natural lemon oil to the citric acid is about 1 to 40. In another embodiment, the weight ratio of the natural lemon oil to the citric acid is about 1 to 80. In a further embodiment, the weight ratio of the natural lemon oil to the citric acid is between 1 to 80 and 1 to 40. Accordingly, because the ratio of the natural lemon oil to citric acid is relatively high (as compared to known lemon-flavored mixes), a relatively small quantity (as compared to known lemon-flavored mixes) of the edible mix can achieve a lemon scent and a lemon taste in a beverage or a food item.

In one embodiment, the edible mix includes granulated maltodextrin, granulated ascorbic acid, and granulated lactose. Maltodextrin is a carbohydrate that is made from corn starch. Granulated maltodextrin may be obtained, for example, from Grain Processing Corporation under the product name M100.

Ascorbic acid, also known as Vitamin C, has the molecular formula of $C_6H_8O_6$. Granulated ascorbic acid may be obtained, for example, from BASF.

Lactose is a carbohydrate found in milk. The molecular formula of lactose is $C_{12}H_{22}O_{11}$. Lactose may be placed in its granulated form by sugar crystalization. Granulated lactose may be obtained, for example, from Protient Corporation.

In one embodiment, the edible mix is produced by disposing an amount of granulated lemon juice solids, an amount of granulated citric acid, an amount of encapsulated natural lemon oil, an amount of granulated maltodextrin, an amount of granulated ascorbic acid, and an amount of granulated lactose within a container, such as a bowl. The components are then mechanically mixed together until the components are in a substantially homogeneous state. In other words, the ingredients are mixed until the entire edible mix is substantially uniform. In one embodiment, the components of the edible mix are manually stirred together. In another embodiment, a mixing machine is used to mix the components of the edible mix.

In another embodiment, the edible mix is produced using an agglomeration method and may be used when cooking or baking certain food items. Specifically, in one embodiment, an amount of granulated lemon juice solids, an amount of granulated citric acid, an amount of granulated maltodextrin, and an amount of granulated ascorbic acid are blended by fluid bed agglomeration.

For example, the granulated lemon juice solids, the granulated citric acid, the granulated maltodextrin, and the granulated ascorbic acid may be sprayed with a binder. In one embodiment, the binder is water (the water will combine with the granulated maltodextrin to act as a binder). Accordingly, the binder will bind the smaller particles, such as the granulated lemon juice solids and the granulated ascorbic acid, to the larger, denser particles, such as the granulated maltodextrin and the granulated citric acid. The agglomerated particles are dried and cooled. In one embodiment, the agglomerated particles are between 0.2 mm and 1.0 mm in size.

An amount of encapsulated natural lemon oil then added to and mixed with the agglomerated ingredients. For example, in one embodiment, an amount of encapsulated natural lemon oil is added to the agglomerated ingredients and the mixture is mechanically mixed together until the components are in a substantially homogeneous state.

The edible mix is disposed in a dispenser for application in a beverage or on a food item. In one embodiment the edible mix is disposed in a single-use packet, similar to a sugar packet. The packaging operation may be accomplished using a conventional machine or method. For example, conventional equipment such as a PDI-IMAR Maxipack SGS8 produced by Packaging Dynamics, Inc. may be used to package the edible mix into single-use packets.

In one embodiment, each single-use packet includes a sufficient amount of edible mix to provide a lemon taste and a lemon scent to a beverage, such as an 16 oz. glass of water. The term "single-use packet" is used herein to mean a packet, such as a sugar packet, made out of paper, plastic, laminated foil or the like, that may be torn or otherwise opened by a user to access the contents of the single-use packet. A single-use packet may be used to apply the edible mix to a beverage or on a food item. For example, in one embodiment, about 0.75 grams of edible mix is packaged in each single-use packet. In another embodiment, each single-use packet includes less than 0.75 grams, for example 0.70 grams, of edible mix. In a further embodiment, each single-use packet includes more than 0.75 grams of edible mix.

In one embodiment, the single-use packet is no greater than 1.5 inches wide and no greater than 2.5 inches tall. The single-use packets containing edible mix may be placed on table with other edible condiments, such as sugar packets. In another embodiment the single-use packet is greater than 1.5 inches wide and greater than 2.5 inches tall.

In another embodiment, the edible mix is disposed in a shaker type dispenser. The shaker type dispenser may be a small shaker type dispenser, similar to a salt or pepper shaker, or a larger shaker type dispenser. In one embodiment, the shaker type dispenser contains more than a single serving of the edible mix. For example, in one embodiment, the shaker type dispenser contains sufficient edible mix to provide a lemon taste and a lemon scent to several glasses of water. The shaker type dispenser may be used to apply the edible mix to a beverage, on a food item, or in a baked or cooked good.

EXAMPLE 1

Eighty nine and five tenths (89.5) grams of an edible mix was produced by mixing the following components: thirty eight (38) grams or 42.5% by weight of the entire edible mix of granulated citric acid; thirty (30) grams or 33.5% by weight of the entire edible mix of lactose; five (5) grams or 5.6% by weight of the entire edible mix of granulated maltodextrin; six and a five tenths (6.5) grams or 7.3% by weight of the entire edible mix of granulated lemon juice solids; seven (7) grams or 8% by weight of the entire edible mix of capsules containing encapsulated natural lemon oil; and three (3) grams or 3.4% by weight of the entire edible mix of ascorbic acid.

In this example, about 90% of the weight of the encapsulated natural lemon oil is the capsule itself. Additionally, an "18+1" granulated lemon juice solid was used. Thus, in this example there is about seventy seven hundredths (0.77) of a gram of natural lemon oil (the encapsulated natural lemon oil and the lemon oil in the granulated lemon juice solid) in the entire edible mix. Accordingly, in this example, the weight of the natural lemon oil is about 0.85% of the total weight of the edible mix. Additionally, in this example the weight ratio of the natural lemon oil to the dehydrated lemon juice (18% of the granulated lemon juice solids) is about 0.65 to 1. Further, in this example, the weight ratio of the encapsulated natural lemon oil to the dehydrated lemon juice is about 0.60 to 1.

As indicated above, about seventy seven hundredths (0.77) of a gram of natural lemon oil and about thirty eight (38) grams of citric acid are present in the edible mix of this example. Accordingly, the weight ratio of natural lemon oil to citric acid in the edible mix of this example is about 1 to 49.

Following this example, the edible mix can optionally be disposed into single use packets. Each of the single use packets includes about 0.75 grams of the edible mix. Specifically, each of the single use packets includes about 0.318 grams of citric acid, 0.251 grams of lactose, 0.042 grams of granulated maltodextrin, 0.054 grams of granulated lemon juice solids, 0.059 grams of capsules containing encapsulated natural lemon oil, and 0.025 grams of ascorbic acid.

EXAMPLE 2

Eighty seven (87) grams of an edible mix was produced by mixing the following components: about thirty six (36) grams or 41.4% by weight of the entire edible mix of granulated citric acid; about thirty (30) grams or 34.5% by weight of the entire edible mix of lactose; about five (5) grams or 5.7% by weight of the entire edible mix of granulated maltodextrin; about six (6) grams or 6.9% by weight of the entire edible mix of granulated lemon juice solids; about seven (7) grams or 8% by weight of the entire edible mix of capsules containing encapsulated natural lemon oil; and about three (3) grams or 3.4% by weight of the entire edible mix of ascorbic acid.

In this example, about 93% of the weight of the encapsulated natural lemon oil is the capsule itself. Additionally, an "18+1" granulated lemon juice solid was used. Thus, in this example there is about fifty five hundredths (0.55) of a gram of natural lemon oil (the encapsulated natural lemon oil and the lemon oil in the granulated lemon juice solid) in the entire edible mix. Accordingly, in this example, the weight of the natural lemon oil is about 0.63% of the total weight of the edible mix. Additionally, in this example the weight ratio of the natural lemon oil to the dehydrated lemon juice (18% of the granulated lemon juice solids) is about 0.51 to 1. Further, in this example, the weight ratio of the encapsulated natural lemon oil to the dehydrated lemon juice is about 0.45 to 1.

As indicated above, about fifty five hundredths (0.55) of a gram of natural lemon oil and about thirty six (36) grams of citric acid are present in the edible mix of this example. Accordingly, the weight ratio of natural lemon oil to citric acid in the edible mix of this example is about 1 to 65.

Following this example, the edible mix can optionally be disposed into single use packets. Each of the single use packets includes about 0.7 grams of the edible mix. Specifically, each of the single use packets includes about 0.290 grams of citric acid, about 0.241 grams of lactose, about 0.040 grams of maltodextrin, about 0.048 grams of granulated lemon juice solids, about 0.056 grams of capsules containing encapsulated natural lemon oil, and about 0.024 grams of ascorbic acid.

EXAMPLE 3

The following components are placed together: 0.25 grams of granulated citric acid; 0.23 grams of granulated maltodextrin; 0.1725 grams of granulated lemon juice solids; and 0.02 grams of granulated ascorbic acid. The components are sprayed with water. The wetted granules are dried and cooled. Three hundredths of a gram (0.03 grams) of capsules containing encapsulated natural lemon oil is mixed with the agglomerated components. The mixture is stirred until the mixture reaches a substantially homogeneous state.

While the invention has been described in detail and with references to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. For example, although edible mix has been described as being packaged in certain types of containers, the edible mix may be packaged in any type and any size of container. Additionally, although the edible mix is discussed as having certain components in certain quantities, the edible mix may contain different components and/or different quantities of the components. Finally, although the edible mix has been described as including encapsulated natural lemon oil, it is not necessary that the edible mix include encapsulated natural lemon oil. For example, the edible mix could include the oil of a citrus fruit and/or natural oil of a citrus fruit encapsulated within a capsule. In another example, the edible mix could include lime oil and/or encapsulated natural lime oil.

What is claimed is:

1. A method of using an edible crystalline composition, comprising:
    adding an edible crystalline composition to a beverage or food item,
        wherein the crystalline composition consists essentially of granulated citric acid or granulated malic acid, encapsulated natural lemon oil, and granulated ascorbic acid.

2. The method of claim 1, wherein the beverage is water or a soft drink.

3. The method of claim 1, wherein the food item is fish or seafood.

4. The method of claim 1, wherein the crystalline composition is added during cooking or baking a food item.

5. A method of using an edible crystalline composition, comprising:
    adding an edible crystalline composition to a beverage or food item,
        wherein the crystalline composition comprises granulated citric acid or granulated malic acid, granulated lime juice solids, encapsulated natural lime oil, and granulated ascorbic acid.

6. The method of claim 5, wherein the beverage is water or a soft drink.

7. The method of claim 5, wherein the food item is fish or seafood.

8. The method of claim 5, wherein the crystalline composition is added during cooking or baking a food item.

9. A method of manufacturing an edible crystalline composition, comprising: mixing granulated citric acid or granulated malic acid, granulated ascorbic acid and encapsulated natural citrus oil, to form a crystalline composition that tastes and smells like fresh citrus.

10. The method of claim 9, further comprising: packaging the mixture in a moisture-free packet.

* * * * *